US008895817B2

(12) United States Patent
Schaffer

(10) Patent No.: US 8,895,817 B2
(45) Date of Patent: *Nov. 25, 2014

(54) METHOD FOR BREEDING TOMATOES HAVING REDUCED WATER CONTENT AND PRODUCT OF THE METHOD

(75) Inventor: Arthur A. Schaffer, Hashmonaim (IL)

(73) Assignee: The State of Israel, Ministry of Agriculture & Rural Development, Agricultural Research Organization (ARO) (Volcani Center), Beit-Dagan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/636,880

(22) Filed: Dec. 14, 2009

(65) Prior Publication Data

US 2010/0095393 A1 Apr. 15, 2010

Related U.S. Application Data

(63) Continuation of application No. 11/506,896, filed on Aug. 21, 2006, now abandoned, which is a continuation of application No. 10/069,389, filed as application No. PCT/IL00/00389 on Jul. 4, 2000, now Pat. No. 7,119,261.

(30) Foreign Application Priority Data

Aug. 19, 1999 (IL) .......................................... 131509

(51) Int. Cl.
*A01H 5/08* (2006.01)
(52) U.S. Cl.
USPC ...................................................... 800/317.4
(58) Field of Classification Search
CPC ....................................................... A01H 5/08
USPC .............................................. 800/260, 317.4
See application file for complete search history.

(56) References Cited

U.S. PATENT DOCUMENTS

| 5,411,561 | A | 5/1995 | Conley |
| 5,434,344 | A | 7/1995 | Bennett et al. |
| 5,557,883 | A | 9/1996 | Walker |
| 5,817,913 | A * | 10/1998 | Schaffer ........................ 800/263 |
| 7,119,261 | B1 * | 10/2006 | Schaffer ..................... 800/317.4 |
| 2004/0003107 | A1 | 1/2004 | Barham et al. |
| 2004/0031072 | A1 | 2/2004 | La Rosa et al. |
| 2007/0022504 | A1 | 1/2007 | Shaffer |
| 2013/0316057 | A1 | 11/2013 | Schaffer et al. |

FOREIGN PATENT DOCUMENTS

| EP | 1211926 | 11/2003 |
| EP | 2131662 | 12/2009 |
| IL | 125425 | 3/1999 |
| WO | WO 00/05390 | 2/2000 |
| WO | WO 01/13708 | 3/2001 |
| WO | WO 2006/030445 | 3/2006 |
| WO | WO 2008/119618 | 10/2008 |

OTHER PUBLICATIONS

North Carolina Agricultural Research Service. PVP 9300161, Jan. 31, 1997.*
Requisition by the Examiner Dated Dec. 22, 2010 from Canadian Intellectual Property Office Re. Application No. 2,382,191.
Response Dated Nov. 1, 2010 to Notification of Reasons for Refusal of Jun. 15, 2010 From the Japanese Patent Office Re. Application No. 2001-517862.
Hovav et al. "The Identification of A Gene (Cwp1), Silencing During Solanum Evoiation. Which Causes Cuticle Microfissuring and Dehydration When Expressed in Tomato Fruit", The Plant Journal, 52: 627-639, 2007.
Translation of Decision of Refusal Dated Jan. 4, 2011 From the Japanese Patent Office Re. Application No. 2001-517862.
Response Dated Apr. 26, 2011 to Decision of Refusal of Jan. 4, 2011 From the Japanese Patent Office Re. Application No. 2001-517862.
Friedmann et al. "A Novel Source of Resistance to Tomato Yellow Leaf Curl Virus Exhibiting a Symptomless Reaction to Viral Infection", Journal of the American Society for Horticultural Science. 123(6): 1004-1007, 1998.
Walkerpeach et al. "Agrobacterium-Mediated Gene Transfer to Plant Cells: Cointegrated and Binary Vector Systems", Plant Molecular Biology Manual, Kluwer Academic Publishers, PMAN-B1/1-PMAN-B1/19. 1994.
Wellesen et al. "Functional Analysis of the LACERATA Gene of Arabidopsis Provides Evidence for Different Roles of Fatty Acid?—Hydroxylation in Devlopment", Proc. Natl. Acad. Sci. USA. 98(17): 9694-9699, Aug. 14, 2001.
Whaley Emmons et al. "Environmental and Physiological Effects on Cuticle Cracking in Tomato", Journal of the American Society of Hort Science, 122(6): 797-801, 1997.
Wilson et al. "Studies on the Cuticle of Tomato Fruit. I. Fine Structure of the Cuticle", Zeitung der Pflanzenphysiolgie, 77: 359-371, 1976.
Yephremov et al. "Characaterization of the FIDDLEHEAD Gene of Arabidopsis Reveals a Link Between Adhesion Response and Cell Differentation in the Epidermis", The Plant Cell. 11: 2187-2201, Nov. 1999.
Young "Cuticle Cracks in Tomato Fruits", Phytopathology, 37: 143-145, 1947.
International Preliminary Report on Patentability Dated Mar. 29, 2007 From the International Burean of WIPO Re.: Application No. PCT/IL2005/001000.
Invitation to Pay Additional Fees Dated Apr. 25, 2006 From the International Searching Authoity Re.: Application No. PCT/IL05/01000.

(Continued)

*Primary Examiner* — Shubo (Joe) Zhou
*Assistant Examiner* — Keith Robinson

(57) ABSTRACT

A method for breeding tomato plants that produce tomatoes with reduced fruit water content including the steps of crossing at least one *Lycopersicon esculentum* plant with a *Lycopersicon* spp. to produce hybrid seed, collecting the first generation of hybrid seeds, growing plants from the first generation of hybrid seeds, pollinating the plants of the most recent hybrid generation, collecting the seeds produced by the most recent hybrid generation, growing plants from the seeds of the most recent hybrid generation, allowing plants to remain on the vine past the point of normal ripening, and screening for reduced fruit water content as indicated by extended preservation of the ripe fruit and wrinkling of the fruit skin.

2 Claims, No Drawings

(56) References Cited

OTHER PUBLICATIONS

Notice of Allowance Dated Dec. 18, 2012 From the US Patent and Trademark Office Re. U.S. Appl. No. 11/663,151.
Office Action Dated Nov. 6, 2011 From the Israel Patent Office Re. Application No. 164125 and Its Translation Into English.
Schoenherr "Water Permeability of Isolated Cuticular Membranes: The Effect of pH and Cations on Diffusion, Hydrodynamic Permeability and Size of Polar Pores in the Cutin Matrix", Planta, 125: 113-126, 1976.
Schoenherr et al. "Water Permeability of Plant Cuticles. Dependence of Permeability Coefficients of Cuticular Transpiration on Vapor Pressure Saturation Deficit", Planta, 144: 391-400, 1979.
Tanksley et al. "High Density Molecular Linkage Maps of the Tomato and Potato Genomes", Genetics, 132: 1141-1160, Dec. 1992.
Todd et al. "KCS1 Encodes A Fatty Acid Elongase 3-Ketoacyl-CoA Aynthase Affecting Wax Biosynthesis in Arabidopsis Thaliana", The Plant journal, 17(2): 119-130, 1999.
Tukey "Observations on the Russeting of Apples Growing in Plastic Bags", Proceedings of the American Society for horticultural Science, 74: 30-39, 1959.
Vogg et al. "Tomato Fruit Cuticular Waxes and Their Effects on Transpiration Barrier Properties: Functional Characterization of a Mutant Deficient in a Very-Long-Chain Fatty Acid ?-Ketoacyl-CoA Synthase", Journal of Experimental Botany, 55(401): 1401-1410, Jun. 2004.
Voisey et al. "Tomato Skin Strength—Its Measurement and Relation to Cracking", Journal of the American Society of Horticultural Science, 95(4): 485-488, 1970.
Millar et al. "CUT1, An Arabidopsis Gene Required for Cuticular Wax Biosynthesis and Pollen Fertility, Encodes a Very-Long-Chain Fatty Acid Condensing Enzyme", The Plant Journal, 11: 825-838, May 1999.
Miron et al. "Sucrose Phosphate Synthase, Sucrose Synthase, and Invertase Activities in Developing Fruit of Lycopersicon Esculentum Mill. and the Sucrose Accumulating Lycopersicon Hirsutum Humb. and Bonpl.", Plant Physiology, 95: 623-627, 1991.
Miron et al. "Sucrose Uptake, Invertase Localization and Gene Expression in Developing Fruit of Lycopersicon Esculentum and the Sucrose-Accumulating Lycopersicon Hirsutum", Physiologia Plantarum, 115: 35-47, 2002.
Monforte et al. "Comparison of a Set of Allelic QTL-NILs for Chromosome 4 of Tomato: Deductions About Natural Variation and Implications for Germplasm Utilization", Theoretical and Applied Genetics, 102: 572-590, 2001.
Nawrath "The Biopolymers Cutin and Suberin", The Arabidopsis Book, American Society of Plant Biologists, p. 1-14, Apr. 4, 2002.
Ojimelukwe "Effects of Processing Methods on Ascorbic Acid Retention and Sensory Charateristics of Tomato Products", Journal of Food Science and Technology, 31(3): 247-248, 1994.
Peet "Fruit Cracking in Tomato", HortTechnology, 2(2): 216-223, Apr./Jun. 1992.
Koorneef et al. "A Genetic and Phenotypic Description of Eceriferum (Cer) Mutants in Arabidopsis Thaliana", Journal of Heredity, 80: 118-122, 1989.
Koske et al. "Influence of Ground Bed Heating and Cultiva on Tomato Fruit Cracking", HortScience, 15(6): 760-762, 1980.
Kunst et al. "Biosynthesis and Secretion of Plant Cuticular Wax", Progress in Lipid Research, 42: 51-80, 2003.
Kurata et al. "The YORE-YORE Gene Regulates Multiple Aspects of Epidermal Cell Differentiation in Arabidopsis", The Plant Journal, 36: 55-66, 2003.
Lownds et al. "Relationships Between Postharvest Water Loss and Physical Properties of Pepper Fruit (Capsicum Annuum L.)", HortScience, 28(12): 1182-1184, 1993.
Mayer et al. "Uncharacterized Protein [Arabidopsis Thaliana]", NCBI GenBank, Version NP_568038.1 GI: 18420207, Accession No. NP_568038, 1999.
Meissner et al. "A New Model System for Tomato Genetics", The Plant Journal, 12(6): 1465-1472, 1997.

Fulton et al. "Advanced Backross QTL Analysis of a Lycopersicon x Lycopersicon Parviflorum Cross", Theoretical Applied Genetics, 100: 1025-1042, 2000.
Fulton et al. "Microprep Protocol for Extraction of DNA From Tomato and Other Herbaceous Plants", Plant Molecular Biology Reporter, 13(3): 207-209, 1995.
Ghosh et al. "Cloning and Sequencing of Potato Virus Y Coat Protein Gene From an Indian Isolate and Development of Transgenic Tobacco for PVY Resistance", Current Science, 82(7): 855-859, Apr. 20, 2002.
Halford et al. "Isolation of a Gene Expressed During Early Embryogenesis From the Region of 22q11 Commonly Deleted in DiGeorge Syndrome", Human Molecular Genetics, 2(10): 1577-1582, 1993.
Holloway "Structure and Histochemistry of Plant Cuticular Membranes: An Overview", The Plant Cuticle, Academic Press, 1-33, 1982.
Hooker et al. "Significance of the Expression of the CER6 Condensing Enzyme for Cuticular Wax Production in Arabidopsis", Plant Physiology, 129: 1568-1580, Aug. 2002.
Kolattukudy "Biopolyester Membranes of Plants: Cutin and Suberin", Science, 208: 990-999, May 30, 1980.
Chen et al. "Cloning and Characterization of the WAX2 Gene of Arabidopsis Involved in Cuticle Membrane and Wax Production", The Plant Cell, 15: 1170-1185, 2003.
Considine et al. "Physical Aspects of Fruit Growth", Plant Physiology, 68: 371-376, 1981.
Cotner et al. "Pericarp Anatomy of Crack-Resistant and Susceptible Tomato Fruits", Journal of the American Society of Horticultural Science, 94: 136-137, 1969.
Dhalluin et al. "Structure and Ligand of a Histone Acetyltransferase Bromodomain", Nature, 399: 491-496, Jun. 3, 1999.
Ehret et al. "Cuticle Cracking in Tomato Fruit", Journal of Horticultural Science, 68(2): 195-201, 1993.
Eshed et al. "An Introgression Line Population of Lycopersicon Pennellii in the Cultivated Tomato Enables the Identification and Fine Mapping of Yield-Associated QTL", Genetics, 141: 1147-1162, Nov. 1995.
Fiebig et al. "Alterations in CER6, A Gene Identical to CUT1, Differentially Affect Long-Chain Lipid Content on the Surface of Pollen and Stems", The Plant Cell, 12: 2001-2008, Oct. 2000.
Aharoni et al. "The SHINE Clade of AP2 Domain Transcription Factors Activates Wax Biosynthesis, Alters Cuticle Properties, and Confers Drought Tolerance When Overexpressed in Arabidopsis", The Plant Cell, 16: 2463-2480, Sep. 2004.
Altschul et al. "Basic Local Alignment Search Tool", Journal of Molecular Biology, 215: 403-410, 1990.
Baker et al. "Composition of Tomato Fruit Cuticle as Related to Fruit Growth and Development", The Plant Cuticle, Academic Press, 33-44, 1982.
Bakker "Russeting (Cuticle Cracking) In Glasshouse Tomatos in Relation to Fruit Growth", Journal of Horticultural Science, 63(3): 459-463, 1988.
Barg et al. "The TYLCV-Tolerant Tomato Line MP-1 is Characterized by Superior Transformation Competence", Journal of Experimental Botany, 48(316): 1919-1923, Nov. 1997.
Blee et al. "Biosynthesis of Cutin Monomers: Involvement of a Lipzygenase/Peroxygenase Pathways", The Plant Journal, 4(1): 113-123, 1993.
Borden "RING Fingers and B-Boxes: Zinc-Binding Protein-Protein Interaction Domains", Biochemistry and Cell Biology, 76(2/3): 351-358, 1998.
Requisition by the Examiner Dated Jan. 25, 2012 From the Canadian Intellectual Property Office Re. Application No. 2,580,713.
Response Dated Sep. 7, 2011 to Official Action of Jul. 7, 2011 From the US Patent and Trademark Office Re. U.S. Appl. No. 11/663,151.
Response Dated Ju. 23, 2011 to Office Action of Feb. 23, 2011 From the Israel Patent Office Re. Application No. 164125.
Response Dated May 26, 2011 to Notice of Reason for Rejection of Jan. 11, 2011 From the Japanese Patent Office Re. Application No. 2007-531955.
Response Dated Dec. 29, 2010 to Office Action of Aug. 29, 2010 From the Israel Patent Office Re. Application No. 164125.

(56) References Cited

OTHER PUBLICATIONS

Translation of Notice of Reason for Rejection Dated Jan. 11, 2011 From the Japanese Patent Office Re. Application No. 2007-531955.
Aarts et al. "Molecular Characterization of the CER1 Gene of Arabidopsis Involved in Epicuticular Wax Biosynthesis and Pollen Fertility", The Plant Cell, 7: 2115-2127, Dec. 1995.
Office Action Dated Jan. 16, 2013 From the Israel Patent Office Re. Application No. 164125 and Its Translation Into English.
Office Action Dated Feb. 23, 2011 From the Israel Patent Office Re. Application No. 164125 and Its Translation Into English.
Office Action Dated Aug. 29, 2010 From the Israel Patent Office Re. Application No. 164125 and Its Translation Into English.
Official Action Dated Jul. 7, 2011 From the US Patent and Trademark Office Re. U.S. Appl. No. 11/663,151.
Official Action Dated Nov. 22, 2011 From the US Patent and Trademark Office Re. U.S. Appl. No. 11/663,151.
Official Action Dated May 23, 2012 From the US Patent and Trademark Office Re. U.S. Appl. No. 11/663,151.
Requisition by the Examiner Dated Jan. 17, 2013 From the Canadian Intellectual Property Office Re. Application No. 2,580,713.
Peet et al. "Role of Excess Water in Tomato Fruit Cracking", HortScience, 30(1): 65-68, Feb. 1995.
Pruitt et al. "FIDDLEHEAD, A Gene Required to Suppress Epidermal Cell Interactions in Arabidopsis, Encodes a Putative Lipid Biosynthetic Enzyme", Proc. Natl. Acad. Sci. USA, 97(3): 1311-1316, Feb. 1, 2000.
Reina et al. "Plant Cutin Biosynthesis: The Involvement of a New Acyltransferase", Trends in Plant Science, 6(7): 296, Jul. 2001.
Riederer et al. "Protecting Against Water Loss: Analysis of the Barrier Properties of Plant Cuticles", Journal of Experimental Botany, 52(363): Plants Under Stress Special Issue: 2023-2032, Oct. 2001.
Sasaki et al. "Unknown Protein<Similar to Oryza Sativa Chromosome 4, OSJNBa0017B10.5 [Oryza Sativa Japonica Group]", NCBI GenBank, Version BAD23681.1, GI: 48716989, Accession No. BAD23681, 2002.
Schnurr et al. "The Acyl-CoA Synthetase Encoded by LACS2 is Essential for Normal Cuticle Development in Arabidopsis", The Plant Cell, 16: 629-642, Mar. 2004.
Schoenherr "Water Permeability of Isolated Cuticular Membranes: The Effect of Cuticular Waxes on Diffusion of Water", Planta, 131: 159-164, 1976.
Requisition by the Examiner Dated May 31, 2012 From the Canadian Intellectual Property Office Re. Application No. 2,382,191.
Response Dated Jun. 20, 2011 to Requisition by the Examiner of Dec. 22, 2010 From the Canadian Intellectual Property Office Re. Application No. 2,382,191.
Response Dated Jun. 22, 2011 to the Requisition by the Examiner of Dec. 22, 2010 From the Canadian Intellectual Property Office Re. Application No. 2,382,191.
Translation of Notification of Reasons for Refusal Dated Oct. 2, 2012 From the Japanese Patent Office Re. Application No. 2011-106718.
Translation of Questioning Dated Feb. 14, 2013 From the Japanese Patent Office Re. Application No. 2001-517862.
Translation of Notification of Reasons for Rejection Dated Sep. 3, 2013 From the Japanese Patent Office Re. Application No. 2001-517862.
Translation of Decision of Rejection Dated Aug. 27, 2013 From the Japanese Patent Office Re. Application No. 2011-106718.
Official Action Dated Mar. 4, 2005 From the United States Patent and Trademark Office Re.: U.S. Appl. No. 10/069,389.
Official Action Dated Feb. 19, 2008 From the US Patent and Trademark Office Re.: U.S. Appl. No. 11/506,896.
Official Action Dated Dec. 30, 2008 From United States Trademark and Patent Office, Re.: U.S. Appl. No. 11/506,896.
Official Action Dated Dec. 30, 2008 From the US Patent and Trademark Office Re.: U.S. Appl. No. 11/506,896.
Requisition by the Examiner Dated Dec. 22, 2010 From the Canadian Intellectual Property Office Re. Application No. 2,382,191.
Bareham "A Word About Genetically Modified Tomatoes", The Big Red Book of Tomatoes, p. 12-13, 1999.

Hovav et al. "The Identification of a Gene (Cwp1), Silencing During Solanum Evolution, Which Causes Cuticle Microfissuring and Dehydration When Expressed in Tomato Fruit", The Plant Journal, 52: 627-639, 2007.
Merriam-Webster "Definition of Species: Colour Photographs of IL 4-4 (Numbered A, B, C and D)", Merriam-Webster OnLine Dictionary, 4 P, 2006.
SGN Solanaceae Genomics Network (SGN), Data Overview (www.sgn.cornell.edu/cgi-bin/content/sgn_data.pl), 2006.
"Colour Photographs of IL 4-4 (Numbered A, B, C and D)", 2 P, 1999.
"Colour Photopraphs of TA517 (Numbered A and B)", 1 P, 1999.
"Molecular Confirmation of IL-4-4", Results of Marker Analysis, 2 P, 1999.
Office Action Dated Jan. 26, 2006 From the Israeli Patent Office Re.: Application No. 131509.
Office Action Dated Mar. 7, 2006 From the Israeli Patent Office Re.: Application No. 131509.
Official Action Dated Aug. 14, 2009 From the US Patent and Trademark Office Re.: U.S. Appl. No. 11/506,896.
Official Action Dated Feb. 19, 2008 From the US Patent and Trademark Office, Re.: U.S. Appl. No. 11/506,896.
Official Action Dated Dec. 2, 2005 From the United States Patent and Trademark Office, Re.: U.S. Appl. No. 10/069,389.
Official Action Dated Mar. 4, 2005 From the United States Patent and Trademark Office, Re.: U.S. Appl. No. 10/069,389.
Opposition Against Patent No. 1211926 Dated Sep. 29, 2006 From the European Patent Office Re.: Application No. 00940724.8.
Requisition by the Examiner Dated Nov. 20, 2008 From the Canadian Intellectual Property Office Re.: Application No. 2,382,191.
Azanza et al. "Characterization of the Effect of Introgressed Segments of Chromosome 7 and 10 From Lycopersion Chmielewskii on Tomato Soluble Solids, PH, and Yield", Theoretical and Applied Genetics, 87: 965-972, 1994.
Azanza et al. "Genes From Lycopersicon Chmielewskii Affecting Tomato Quality During Fruit Ripening", Theoretical and Applied Genetics, 91: 495-504, 1995.
Baker et al. "Composition of Tomato Fruit Cuticle as Related to Fruit Growth and Development", Long Ashton Research Station, University of Bristol, 1982.
Bareham "The Big Red Book of Tomatoes", 1999. Abstract.
Bernacchi et al. "Advanced Backcross QTL Analysis in Tomato. I. Identification of QTLs for Traits of Agronomic Importance From Lycopersicon Hirsutum", Theoretical and Applied Genetics, 97: 381-397, 1998.
Bernacchi et al. "Advanced Backcross QTL Analysis of Tomato. II. Evaluation of Near-Isogenic Lines Carrying Single-Donar in Introgressions for Desirable Wild QTL-Alleles Derived From Lycopersicon Hirsutum and L. Pimpinelliifolium", Theoretical and Applied Genetics, 97: 170-180, 1998.
Davies et al. "The Constituents of Tomato Fruit—The Influence of Environment, Nutrition, and Genotype", CRC Critical Reviews in Food Science and Nutrition, 15(3): 204-277, 1981.
Davis "Occurrence of Sucrose in the Fruit of Some Species of Lycopersicon", Nature, 209(5023): 640-641, 1966.
Eshed et al. "A Genomic Library of Lycopersicon Pennellii in L. Esculentum: A Tool for Fine Mapping of Genes", Enphytica, 79: 175-179, 1994.
Eshed et al. "An Introgression Line Population of Lycopersicon Pennellii in the Cultivated Tomato Enables the Identification and Fine Mapping of Yield-Associated QTL", Genetics, 141: 1147-1162, 1995.
Eshed et al. "Introgressions From Lycopersicon Pennellii Can Improve the Soluble-Solids Yield of Tomato Hybrids", Theoretical and Applied Genetics, 88: 891-897, 1994.
Frary et al. "Advanced Backcross QTL Analysis of a Lycopersicon Esculentum XL. Pennellii Cross and Identification of Possible Orthologs in the Solanaceae", Theoretical and Applied Genetics, 108: 485-496, 2004.
Fulton et al. "Advanced Backcross QTL Analysis of a Lycopersicon Esculentum X Lycopersicon Parviflorum Cross", Theoretical and Applied Genetics, 100: 1025-1042, 2000.

(56) References Cited

OTHER PUBLICATIONS

Golias et al. "Resistance of Tomato Cultivars to Fruit Cracking", Acta Universitatis Agriculturae, (Facultas Agronomica), 32(4): 201-208, 1984. Abstract.
Grierson et al. "Fruit Riping and Quality", Chap.6: 242-280, 1986.
Hovav et al. "Map-Based Cloning of a Gene (CWP) That Controls Cuticulat Permeability in Mature Tomato Fruit", Department of Vegetable Crop, Agriculture Organization, Volcani Center, IL, 1999.
Hyde "The New Rural Industries, A Handbook for Farmers and Investors", p. 229-230, 1997.
Martin et al. "The Physical Factors Involved in the Drying of Sultana Grapes", p. 444-459, 1957.
Moyle et al. "Genetics of Hybrid Incompatibility Between Lycopersicon Esculentum and L. Hirsutum", Genetics, 169: 355-373, 2005.
Nesbitt et al. "Comparative Sequencing in the Genus Lycopersicon: Implications For the Evolution of Fruit Size in the Domestication of Cultivated Tomatoes", Genetics, 162: 365-379, 2002.
Nir et al. Comparison of Promoter Regions of Vacuolar Invertase From Green-Fruited, Sucrose-Accummulating and Red-Fruited, Hexose-Acccumulating Lycopersicon Species, Department of Vegetable Crop, Agriculture Organization, Volcani Center, IL, 1999.
Nury et al. "Fruits", Food Dehydration, 2(Chap.11): 158-198, 1973.
Ojimelukwe "Effects of Processing Methods on Ascorbic Acid Retention and Sensory Characterics of Tomato Products", Journal of Food Science and Technology, 31(3): 247-248, 1994.
Schaffer et al. "Modification of Carbohydrate Content in Developing Tomato Fruit", HortScience, 34(6): 1024-1027, 1999.
SGN "COSII Marker C2_At1g27530 (SGN-M6724)", SOL Genomics Network, Cornell University, 10 P, 1999.
SGN "Map of Chromosome 4: Tomato-EXPEN 2000", SOL Genomics Network, Cornell University, 2 P, 1999.
SGN Solanaceae Genomics Network (SGN), Data Overview (www.sgn.cornell.edu/cgi-bin/content/sgn_data.pl), 1999.
Tanksley et al. "Advanced Backcross QTL Analysis in a Cross Between an Elite Processing Line of Tomato and Its Wild Relative L. Pimpinellifolium", Theoretical and Applied Genetics, 92: 213-224, 1996.
University of Florida "Tomato Genetics Cooperative Report", University of Florida, 54: 1, 52, 62, 2004.
Yousef et al. "Evaluation of Breeding Utility of a Chromosomal Segment From Lycopersicon Chmielewskii That Enhances Cultivated Tomato Soluble Solids", Theoretical and Applied Genetics, 103: 1022-1027, 2001.
Summons to Attend Oral Proceedings Pursuant to Rule 115(1) EPC Dated Mar. 10, 2014 From the European Patent Office Re. Application No. 08717525.3
Translation of Notification of Reasons for Refusal Dated Jun. 15, 2010 From the Japanese Patent Office Re. Application No. 2001-517862.
Summons to Oral Proceedings Pursuant to Rule 115(1) EPC Dated Jun. 25, 2014 From the European Patent Office Re. Application No. 00940724.8.

* cited by examiner

METHOD FOR BREEDING TOMATOES HAVING REDUCED WATER CONTENT AND PRODUCT OF THE METHOD

RELATED APPLICATIONS

This Application is a US Continuation of U.S. patent application Ser. No. 11/506,896, filed on Aug. 21, 2006, which is a US Continuation of U.S. patent application Ser. No. 10/069,389, filed on Jul. 1, 2002 which is a US National Phase of PCT Patent Application No. PCT/IL00/00389, filed on Jul. 4, 2000, which claims the benefit of Israel Patent Application No. 131509, filed on Aug. 19, 1999. The contents of the above Applications are all incorporated herein by reference.

FIELD OF THE INVENTION

The present invention relates to a method for breeding tomatoes having reduced water content and/or with the trait of drying while still attached to the vine, and to tomatoes having reduced water content and to products of the method.

BACKGROUND OF THE INVENTION

Dehydrated tomato products comprise an important portion of the tomato industry. The production of tomato pastes, ketchup and other processed tomato products is dependent on the energy-requiring steps of dehydration. The production of "sun-dried" tomato products consists of dehydrating cut tomato fruit either in the sun or in drying ovens.

Dry matter content of mature tomato fruit can range from approximately 5-10% (Davies, J. N. and Hobson, G. E. 1981. The constituents of tomato fruit—the influence of environment, nutrition and genotype. CRC Critical Reviews in Food Sci and Nutr. 15:205-280), depending largely on fruit size. Generally, processing tomato cultivars produce mature fruit with a higher water content of approximately approximate 94-95%. Smaller, "cherry"-type tomato fruit, with a fresh weight of 10-20 grams frequently have higher concentration of solids (dry weight) and hence reduced water concentrations of approximately 90% (10% dry weight).

Generally, tomato fruit development stages can be classified as the pre-climacteric stage, which is comprised of the early stages of fruit growth until incipient ripening, the climacteric stage and the post-climacteric or senescent stage. Once the fruit is fully ripe, tissue disorganization occurs, with pathogens contributing to the tissue disorganization, and characteristics associated with "overripening" and subsequent rotting of the fruit become apparent (Grierson, D. and Kader, A. A. 1986. Fruit ripening and quality. In: Atherton, J. G. and Rudich, J. Eds.: The Tomato Crop. Chapman and Hall, London, pp. 241-280).

The production of raisins from grape berries (Vitis vinifera) is a well known process in which the dehydration process occurs by diffusion of water through a waxy cuticle (Martin, R. J. L. and Scott, G. L. 1957. The physical factors involved in the drying of Sultana grapes. Australian Journal of Agricultural Research. 8:444-459). For whole grape berries, the drying process is generally assisted by various dipping treatments of the berry, such as the soda-dip method (Nury, F. S., Brekke, J. E. and Bolin, H. R. 1973. Fruits. In: Van Arsdel, W. B., Copley, M. J. and Morgan, A. I., Eds: Food Dehydration. Avi Publishing Co., Westport, Conn. vol. 2, pp. 158-198). In brief, in this method the berries are dipped in a 0.2-0.3% solution of caustic soda (sodium hydroxide) at a temperature of about 200° F. for a few seconds and are then rinsed with cold water before dehydration. The purpose of the dipping is to modify the berry cuticle so that transpiration of water vapor across the cuticle may proceed at a faster rate. The tomato, like the grape, is botanically classified as a berry and has a waxy cuticle on the fruit epidermis (Baker, E. A., Bukovac, M. J. and Hunt, G. M. 1982. Composition of tomato fruit cuticles as related to fruit growth and development. In: Cutler, D. F., Alvin, K. L. and Price, C. E., Eds: The Plant Cuticle. Academic Press, London. pp. 33-44). However, tomatoes will generally undergo degradation if they remain on the vine after ripening. In the case of tomatoes, the harvested fruit is generally cut in half in order to increase the dehydration rate. Alternatively, whole fruit may be pierced in order to facilitate fluid movement (Ojimelukwe, P. C. 1994. Effects of processing methods on ascorbic acid retention and sensory characteristics of tomato products. J. Food Sci. Technol. 31:247-248). Drying of the slices or pierced tomato fruit may take place either in the sun or in various forms of drying ovens based on non-solar energy input.

There are disadvantages to sun-drying since it depends on weather conditions and inclement weather leads to losses. Similarly, there are disadvantages to the use of drying ovens as these are energy consuming. Both sun drying and oven drying may lead to losses in food quality. For example, levels of ascorbic acid; one of the major nutritional contributions of tomatoes in the human diet, decrease significantly in response to sun-drying or oven-drying (Ojimelukwe, P. C. 1994. Effects of processing methods on ascorbic acid retention and sensory characteristics of tomato products. J. Food Sci. Technol. 31:247-248). Furthermore, the necessity to cut the tomato fruit in half before the drying process does not allow for the production of whole dried tomato fruit.

Wild species of the genus Lycopersicon, such as L. hirsutum, may contain within their genetic makeup expressed characteristics not generally present within the L. esculentum species. These genetic traits may be transferred to the cultivated L. esculentum. For example, the genetic trait of sucrose accumulation is present in mature fruit of the subgenus Eriopersicon (including L. hirsutum, L. chmiliewskii and L. peruvianum) and this trait has been transferred to L. esculentum, using classical genetic breeding techniques, as well as molecular genetic techniques (Schaffer, A. A., Petreikov, M., Miron, D., Fogelman, M., Spiegelman, M., Bnei-Moshe, Z., Shen, S., Granot, D., Hadas, R., Dai, N., Levin, I., Bar, M., Friedman, M., Pilowsky, M., Gilboa, N. and Chen, L. 1999. Modification of carbohydrate content in developing tomato fruit. Hortscience 34:1024-1027). The wild species of Lycopersicon, however, may also serve as a source of unexpressed genetic traits that can contribute to the value of cultivated plants (Bernacchi, D., Beck-Bunn, T., Eshed, Y., Lopez, J., Petiard, V., Uhlig, J., Zamir, D. and Tanksley, S. 1998. Advanced backcross QTL analysis in tomato. Identification of QTLs for traits of agronomic importance from Lycopersicon hirsutum. Theor. Appl. Genet. 97:381 397).

SUMMARY OF THE INVENTION

The present invention seeks to provide a method for breeding tomatoes having fruit that naturally dehydrate while still attached to the tomato plant and thus have a reduced water content, and to tomatoes having reduced water content and to products of the method.

The development of tomato varieties with the trait of naturally dehydrating while still attached to the vine, without the accompaniment of degradative processes leading to fruit breakdown is highly valuable to the various components of the tomato industry. It can contribute to reduction of processing costs and energy expenditures in the production of pastes, sauces and ketchups. It can contribute to the production of high quality dried and semi-dried (raisin-type) tomato products. It can contribute to the improvement of tomato fruit transport since the volume of transported material will be decreased. It can improve the storage ability of the tomato fruit since reduced water content will be accompanied by increased soluble solids concentration which contributes to the resistance to microbial spoilage.

There is thus provided in accordance with a preferred embodiment of the present invention a method for breeding tomato plants that produce tomatoes with reduced fruit water content including the steps of crossing at least one *Lycopersicon esculentum* plant with a *Lycopersicon* spp. to produce hybrid seed, collecting the first generation of hybrid seeds, growing plants from the first generation of hybrid seeds, pollinating the plants of the most recent hybrid generation, collecting the seeds produced by the most recent hybrid generation, growing plants from the seeds of the most recent hybrid generation, allowing plants to remain on the vine past the point of normal ripening, and screening for reduced fruit water content as indicated by extended preservation of the ripe fruit and wrinkling of the fruit skin.

In accordance with a preferred embodiment of the present invention the steps of pollinating, collecting the seeds, and growing plants are repeated at least once.

Further in accordance with a preferred embodiment of the present invention the step of pollinating includes self pollination.

Still further in accordance with a preferred embodiment of the present invention the step of pollination includes back crossing with a *Lycopersicon esculentum* plant.

Additionally in accordance with a preferred embodiment of the present invention the *Lycopersicon* spp plant is a *Lycopersicon hirsutum* plant.

In accordance with a preferred embodiment of the present invention the method additionally includes the steps of crossing plants derived from hybrid seeds whose progeny show reduced fruit water content with a *Lycopersicon* plant, growing the crossed plants, and selecting plants with tomato fruits having an increased dry weight percentage as compared to fruit from a non-crossed *Lycopersicon*. The steps of crossing and selecting may be repeated at least once. The crossing may include sexual or asexual crossing. The asexual crossing may include somatic cell hybridization.

Further in accordance with a preferred embodiment of the present invention the method additionally includes the step of propagating the plants with tomato fruits having the desired characteristics. The step of propagating may include vegetative propagation or propagation by seed.

In accordance with a preferred embodiment of the present invention the method additionally includes the steps of crossing plants derived from hybrid seeds whose progeny show reduced fruit water content with a *Lycopersicon* plant, growing the crossed plants, harvesting ripe tomato fruits before signs of dehydration thereof, and allowing the fruits to dehydrate after removal from the plant.

There is also provided in accordance with a preferred embodiment of the present invention a tomato fruit characterized by a capability of natural dehydration while on a tomato plant, natural dehydration being defined as wrinkling of skin of the tomato fruit when the fruit is allowed to remain on the plant after a normal ripe harvest stage, the natural dehydration being generally unaccompanied by microbial spoilage.

There is also provided in accordance with a preferred embodiment of the present invention a tomato fruit characterized by an untreated skin which permits dehydration of the fruit so as to obtain wrinkling of the skin, the dehydration being generally unaccompanied by microbial spoilage.

DETAILED DESCRIPTION OF PREFERRED EMBODIMENTS

Reference is now made to a method for breeding tomatoes having fruit that naturally dehydrate while still attached to the tomato plant and reduced water content.

The method for breeding tomato plants includes first hybridizing at least one *Lycopersicon esculentum* plant with a wild *Lycopersicon* spp. plant. The fruits of the *L. esculentum* plants are then allowed to ripen and the hybrid ($F_1$) seeds are collected. The collected $F_1$ seeds are then planted and $F_1$ plants are grown and allowed to self-pollinate. Selfing may be continued for at least one additional generation or the F1 plants may be crossed to a *L. esculentum* parental plant. Fruits from selfed or backcrossed generations are allowed to remain on the vine past the point of normal ripening, as determined by change of fruit color, and screened for the presence of natural dehydration. Natural dehydration, or reduced water content, is indicated by the wrinkling of the fruit skin when the fruit is allowed to remain on the vine after the normal red ripe harvest stage.

Plants from any of the selfed generations may be propagated for use by vegetative propagation methods such as micropropagation or by sexual propagation methods. The plants may also be crossed with other *L. esculentum* cultivars to create varieties that incorporate characteristics other than reduced fruit water content. The varieties may then be propagated by vegetative or sexual propagation methods.

Plants from any of the selfed generations may also be back crossed to *L. esculentum* for at least one generation. The fruits of the last back cross generation are allowed to remain on the vine past the normal point of ripening. The appearance of dehydration as evidenced by wrinkling of the fruit skin indicates reduced water content in the fruit. Plants selected for this trait may then be propagated either vegetatively or by seed based propagation. Selected plants may then also be crossed with other *L. esculentum* cultivars to create varieties that incorporate characteristics other than reduced fruit water content. The varieties may then also be propagated by vegetative or sexual propagation methods.

Reference is now made to the following example that illustrates the invention.

Example 1

Plants of the *L. esculentum* breeding line 1630 (a Volcani Institute male sterile breeding line, used to simplify the production of the interspecific hybrid) were pollinated with pollen of the wild species *L. hirsutum* (LA1777). Hybrid F1 plants were grown and allowed to self-pollinate, generating F2 seed. F2 seed were sown and about 350 plants were grown in a screenhouse and allowed to self-pollinate. Ripe fruit from each individual plant that produced fruit were individually analyzed for soluble solids (refractometrically) to insure the lines also included the characteristic of high soluble solids. Only 25 of the interspecific F2 plants freely produced fruit. Three F2 plants were selected based on their high sugar content (Brix in excess of 10) when ripe. For example, fruit of F2-82 had 71 mg soluble sugar, composed of sucrose, glucose and fructose, per gram fresh weight of fruit, as determined by the method described herein below. F3 seeds were sown and ten plants of each of the F3 plants of these three F2 selections (termed F2-24, F2-82 and F2-134) were grown, and fruit was allowed to remain on the vine past the normal stage of ripening and harvest. Fruit from these F3 plants were generally yellow when ripe and did not turn red even after the normal ripening stage. Among the F3 plants one plant (F3-203-10, derived from F2-134) showed the characteristic of signs of fruit dehydration, evidenced by wrinkling of the fruit skin.

A pedigree breeding program was developed to obtain tomatoes with reduced water content using as a selection system signs of fruit dehydration as evidenced by wrinkling of the fruit skin after the red ripe stage. This breeding strategy consisted of selfing F3-203-10 until the F4 generation and backcrossing to L. esculentum breeding line L-27, with the product of this cross being selfed for four additional generations to produce the BC1F4 population. Lines of this population (lines 901 and 903) as well as hybrid plants derived from crosses between this population and commercial tomato cultivars (cv. F139 and cv. BR124) produced plants that all showed the trait of fruit dehydration as evidenced by wrinkling of the ripe fruit skin. The presence of the trait in the hybrid plants indicates that the trait is heritable, governed by dominant genetic factors, and can be selected for in the early generations of the breeding program.

Example 2

Pollen from one plant (F2-82) which was characterized by high soluble sugar level in the mature fruit (71 mg soluble sugar, composed of sucrose, glucose and fructose, per gram fresh weight of fruit) was used to pollinate two standard, industry type tomatoes (breeding lines A701 and 699) for the production of two backcross-F1 (BC-F1) populations. One-hundred BC-F2 plants from each of the two hybrids were grown and the presence of signs of fruit dehydration, evidenced by wrinkling of the fruit skin, were seen in fruit of plants from these F2 populations. This shows that even at early stages of a selection program, the trait can be selected for without large populations of plants.

Experiment 3

Fruit of progeny of advanced lines derived from the lines described in experiment 1, that showed the characteristic to dehydrate on the vine, as evidenced by the wrinkling of the fruit were harvested and the juice pressed and Brix of the expressed juice was measured by a digital refractometer (Atago model X-1). The following table shows characteristic Brix values of some of the partially dehydrated tomato fruit (cherry size, approx. 15 g). Fruit were harvested when partially wrinkled but not fully dehydrated. The results of this experiment indicate that the trait of fruit dehydration and increase in Brix value is a selectable inherited trait. The parental selection (self of 1465-3) was partially dehydrated as was the F1 hybrid between 1465-3 and the cherry cultivar F139. This indicates that the trait is at least partially dominant in its inheritance pattern. Similarly, 3 representative plant selections from the F2 population (1730) derived from the self of the F1 (1465-3×F139) which showed the trait of fruit wrinkling are presented and indicates that the selection method can be used in the segregating F2 population.

TABLE 1

Brix values of partially dehydrated tomato fruit, harvested from the vine at the stage when fruit wrinkling was visually observable.

| tomato plant | cross | generation | Brix |
|---|---|---|---|
| 1630-1+2 | 1465-3 self | BC2F2 | 19.2 |
| 1631-1 | 1465-3 x cv. 139 | BC3F1 | 17.4 |
| 1730-3 | 1631-2 self | BC3F2 | 22.4 |
| 1730-4 | 1631-2 self | BC3F2 | 29.0 |
| 1730-5 | 1631-2 self | BC3F2 | 11.1 |

Fruit size was of the cherry-tomato size (approx. 10-15 gr).

Experiment 4

In an experiment to determine whether the dehydration process can take place after removal from the vine, red ripe fruits from a BCF3 population were harvested, as above, and allowed to remain and dehydrate on netted screens on the laboratory bench without temperature control. After approximately one month the fruit had reached 86.2% dry weight, and were generally unaccompanied by microbial spoilage. Percent dry weight was calculated as the percentage of weight after drying in a forced air oven at 60° C. for 24 overnight, compared to the weight of fruit prior to oven drying. Ten representative fruit were used to calculate the percent dry weight.

Such fruit has been maintained for over a year at 5° C. and at room temperature in an uncontrolled environment for at least 5 months, without further decay. The results of these experiments indicate that the dehydrated fruit may be harvested at various stages of dehydration (even before dehydration commences) and that dehydration of the fruit may also continue after detachment from the vine.

Experiment 5

In order to characterize the development of the dehydration process an experiment was carried out in which 14 red-ripe fruit from plants which showed the trait of dehydration of the fruit, but which themselves had not yet reached the dehydration stage, were selected. Seven of these fruit were harvested when red-ripe and analyzed immediately, as described below. The other seven fruit were allowed to remain attached to the vine for an additional 14 days and, when fruit wrinkling was observed, were analyzed, as follows.

Each fruit was individually weighed, a sample of the fruit juice was tested by refractometer, for Brix value. An additional sample of each fruit was weighed fresh and then dried in an oven, as described above, for the calculation of percent dry weight. A third portion of each fruit was used for the analysis of individual soluble sugar levels, as follows.

Individual fruits were harvested and a portion of the fruit pericarp was placed in 80% ethyl alcohol and heated to 70° C. in order to stop enzymatic activity and extract the soluble sugars. Soluble sugars were extracted three times in successive changes of 80% alcohol which was then evaporated.

The sugars were then dissolved in double distilled water, centrifuged at 5,000 rpm in an eppendorf centrifuge tube for 15 minutes to remove cell debris and 0.5 ml aliquot passed through a 0.45 micron filter in preparation for high Pressure Liquid Chromatography (HPLC) analysis. HPLC analysis was performed using a BioRad (Richmond, Calif., USA) Fast Carbohydrate column for the separation of glucose, fructose and sucrose according to the manufacturer's instructions. The sugars were identified and quantified according to chromatographic behavior of standards for the sugars which were obtained from Sigma (St. Louis, Mo., USA).

The results of this study are shown in Table 2 and show that the wrinkling phenomenon is accompanied by loss of water from the fruit, leading to an increase in % dry weight, an increases in Brix and individual sugar concentrations. The dry matter per fruit remains approximately the same. This indicated that the phenomenon of fruit wrinkling, and the concomitant increase in sugar concentration and in dry matter concentration is primarily one of natural dehydration of the fruit, without a concomitant loss of fruit dry matter content.

TABLE 2

| Trait | Red ripe | Wrinkled |
| --- | --- | --- |
| Fresh weight (g/fruit) | 16.63 | 12.20 |
| Percent dry weight | 12.53 | 17.89 |
| Brix | 11.51 | 14.57 |
| Sugars (mg/gm fr w) | | |
| Total | 66.4 | 86.4 |
| Sucrose | 3.8 | 6.1 |
| Glucose | 30.5 | 38.4 |
| Fructose | 32.1 | 41.9 |
| Water content (g/fruit) | 14.55 | 10.02 |
| Dry weight (g/fruit) | 2.08 | 2.18 |
| Sugars (g/fruit) | 1.10 | 1.05 |

In summary, with the methods of the present invention, a tomato fruit can be obtained characterized by an untreated skin, which permits dehydration of the fruit so as to obtain wrinkling of the skin, wherein the dehydration is generally unaccompanied by microbial spoilage. In another aspect of the invention, a tomato fruit can be obtained characterized by a capability of natural dehydration while on a tomato plant, natural dehydration being defined as wrinkling of skin of the tomato fruit when the fruit is allowed to remain on the plant after a normal ripe harvest stage, wherein the natural dehydration is generally unaccompanied by microbial spoilage.

Alternatively, it is noted that the tomato fruit can be treated with a substance, such as sulfur dioxide, to help retain skin color during and after dehydration, such as is done with dried fruits such as raisins.

It will be appreciated by persons skilled in the art that the present invention is not limited to what has been particularly shown and described herein above. Rather the scope of the present invention is defined only by the claims which follow:

What is claimed is:

1. A tomato product comprising a dried or semi-dried tomato fruit which comprises a genome of the *Lycopersicon esculentum* species, wherein said genome comprises an introgression from *Lycopersicon hirsutum* line LA1777, said introgression allowing natural fruit dehydration which results in skin wrinkling of the tomato fruit, wherein a fructose/glucose ratio of said dried or semi-dried tomato fruit is about 1.

2. The tomato product of claim 1 selected from the group consisting of a paste, a sauce and a ketchup.

* * * * *